(12) United States Patent
Walde et al.

(10) Patent No.: US 6,300,753 B1
(45) Date of Patent: Oct. 9, 2001

(54) CIRCUIT FOR A NOX MEASUREMENT SENSOR

(75) Inventors: Tim Walde, Regensburg; Eric Chemisky, Haar, both of (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 09/511,814

(22) Filed: Feb. 24, 2000

(30) Foreign Application Priority Data

Feb. 24, 1999 (DE) .............................................. 199 07 947

(51) Int. Cl.$^7$ .................................................. G01N 27/00
(52) U.S. Cl. .................... 324/71.1; 324/378; 324/425; 204/424
(58) Field of Search .................................... 324/425, 439, 324/444, 71.1, 378; 204/424, 425, 426; 205/781

(56) References Cited

U.S. PATENT DOCUMENTS 6,214,207 * 4/2001 Miyata et al. ....................... 205/781

OTHER PUBLICATIONS

"Performance of Thick Film NOx Sensor on Diesel and Gasoline Engines", Nobuhide Kato et al., Society of Automotive Engineers, Inc., Publication No. 970858, 1997, pp. 199–206.

"Thick Film ZrO2 NOx Sensor for the Measurement of Low NOx Concentration", Nobuhide Kato et al., Society of Automotive Engineers, Inc., Publication No. 980170, 1998, pp. 69–77.

* cited by examiner

Primary Examiner—Safet Metjahic
Assistant Examiner—E P LeRoux
(74) Attorney, Agent, or Firm—Herbert L. Lerner; Laurence A. Greenberg; Werner H. Stemer

(57) ABSTRACT

A circuit for a NOx concentration sensor includes two connected measurement cells disposed in a solid-state electrolyte, a first circuit configuration that, by tapping off a first Nernst voltage (first reference variable), establishes in the cell an oxygen concentration that differs from that in a measured gas, a second circuit configuration that, by tapping off a second Nernst voltage (second reference variable), establishes in the cell an oxygen concentration that differs from that in the first cell, a third circuit configuration that, by tapping off a third Nernst voltage (third reference variable), drives a pump current of oxygen ions that originate from NOx, out of the second cell, a conditioning circuit, and a digital controller. The Nernst voltage is fed to the controller through the conditioning circuit, which shifts and amplifies the voltage such that the reference variable lies in a range around the control point of the controller, and a reference potential of a conditioned Nernst voltage equals that of the controller. The Nernst voltages, being previously preprocessed by the conditioning circuit, are used as a reference variable for regulating the oxygen ion pump current, which amplifies and shifts the Nernst voltages. As a result, a microcontroller with an 8-bit A/D converter can be employed, and A/D ports are saved.

3 Claims, 2 Drawing Sheets

CIRCUIT FOR A NOX MEASUREMENT SENSOR

BACKGROUND OF THE INVENTION

1. Field of the Invention

The invention lies in the field of fluid sensors. The invention relates to a circuit for a NOx measurement sensor.

In order to measure the NOx concentration in a gas, for example in the exhaust gas of an internal combustion engine, it is conventional to employ a thick-layer measurement sensor. Such a measurement sensor is described, for example, in the publication by N. Kato et al., "Thick Film $ZrO_2$ NOx Sensor for the Measurement of Low NOx Concentration", Society of Automotive Engineers, Publication number 980170, 1989, or in N. Kato et al., "Performance of Thick Film NOx Sensor on Diesel and Gasoline Engines", Society of Automotive Engineers, publication number 970858, 1997. The measurement sensor has two measurement cells and is composed of a zirconium oxide that conducts oxygen ions. The sensor implements the following measurement concept: in a first measurement cell, to which the gas to be measured is fed through a diffusion barrier, a first oxygen concentration is established by a first oxygen ion pump current, the intention being that no decomposition of NOx takes place. In a second measurement cell, which is connected to the first cell through a diffusion barrier, a second oxygen ion pump current lowers the oxygen content further. The decomposition of NOx at a measurement electrode leads to a third oxygen ion pump current, which is a measure of the NOx concentration. The entire measurement sensor is brought to an elevated temperature, for example 750° C., by an electric heater.

In order to establish the oxygen ion pump currents, the Nernst voltage is tapped off in the respective measurement cells. Digital microcontrollers are typically employed for the controllers. Two A/D ports on the A/D converter of the microcontroller are needed for one Nernst voltage because the voltage can be measured only with respect to the reference potential of the microcontroller. Accordingly, the voltage across the measurement electrode is typically measured with respect to the reference potential of the microcontroller. In addition, the voltage across the reference electrode is measured with respect to the reference potential of the microcontroller. The Nernst voltage is obtained by forming the difference between these two voltages. If an 8-bit converter and 5 V range are employed, the resolution is then 20 mV. However, the accuracy of the detection of the reference variable is inadequate in the control loop.

Therefore, microcontrollers with 10-bit converters are needed. Such microcontrollers are relatively expensive and available only in a few models. As such, the choice for the production or configuration is restricted.

SUMMARY OF THE INVENTION

It is accordingly an object of the invention to provide a circuit for a NOx measurement sensor that overcomes the hereinafore-mentioned disadvantages of the heretofore-known devices of this general type and that detects a NOx concentration in a gas while avoiding the difficulties and disadvantages resulting from the detection of the Nernst voltage.

With the foregoing and other objects in view, there is provided, in accordance with the invention, a circuit for a measurement sensor detecting a NOx concentration in a gas, including a first measurement cell, a second measurement cell connected to the first measurement cell, the first and second measurement cells disposed in a solid-state electrolyte, a first circuit configuration tapping off a first Nernst voltage serving as a first reference variable for establishing an oxygen concentration in the first measurement cell differing from an oxygen concentration in a gas to be measured, a second circuit configuration tapping off a second Nernst voltage serving as a second reference variable for establishing an oxygen concentration in the second measurement cell differing from an oxygen concentration in the first measurement cell, a third circuit configuration tapping off a third Nernst voltage serving as a third reference variable for driving a pump current of oxygen ions originating from NOx out of the second measurement cell, at least one conditioning circuit, and at least one digital controller having at least one control point, at least one of the first, second, and third Nernst voltages being fed to the at least one controller through the at least one conditioning circuit for shifting and amplifying the at least one of the first, second, and third Nernst voltages such that at the at least one controller at least one of the first, second, and third reference variables lies in a range around the at least one control point of the at least one controller, and a reference potential of a conditioned at least one of the first, second, and third Nernst voltages equals that of the at least one controller.

According to the invention, a conditioning circuit conditions the Nernst voltage tapped off before it is fed to the microcontroller. The conditioning circuit amplifies the Nernst voltage and shifts it such that it is fed to the A/D port of the digital controller in a range around the control point of the controller. Given a gain of, for example, a factor of 10, the range of interest of about 500 mV is widened to 5 V and shifted. As a result, even using an 8-bit converter, a resolution of, for example, 2 mV can be achieved.

Such resolution is adequate for the reference variable. The conditioning circuit is advantageously constructed as an analog circuit, which performs both the formation of the difference between the voltages across the measurement electrode and the reference electrode and also performs the shifting and the amplification. Depending on the configuration of the circuit, the shift is made in either a positive or negative voltage direction.

In accordance with another feature of the invention, the at least one conditioning circuit includes an output, an electrode, a reference electrode, an operational amplifier with an operational amplifier output connected to the output, a conditioned at least one of the first, second, and third Nernst voltages being present at the output, an inverting input, and a non-inverting input, a first resistor connected to the inverting input and to the electrode for tapping off a first potential, a second resistor connected to the inverting input and to the operational amplifier output, a third resistor connected to the non-inverting input and to the reference electrode, and a fourth resistor connected to the non-inverting input and to ground.

In accordance with a concomitant feature of the invention, the at least one controller has at least one A/D converter converting a conditioned at least one of the first, second, and third Nernst voltages from analog to digital with 8-bit resolution.

The configuration results in a two-part advantage, on one hand, one A/D port on the A/D converter of the digital controller is saved, and, on the other hand, a cost-effective 8-bit converter is adequate for use.

Other features that are considered as characteristic for the invention are set forth in the appended claims.

Although the invention is illustrated and described herein as embodied in a circuit for a NOx measurement sensor, it is nevertheless not intended to be limited to the details shown, because various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DESCRIPTION OF THE PREFERRED EMBODIMENTS

Figure 1:
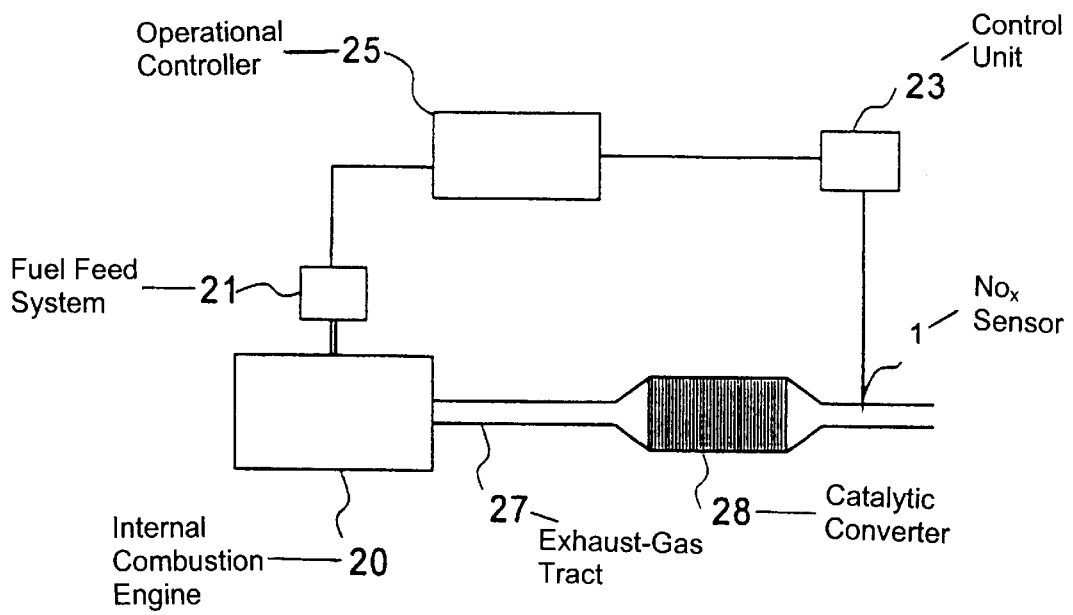
FIG. 1 is a block diagram of an internal combustion engine including a NOx measurement sensor according to the invention.

In all the figures of the drawing, sub-features and integral parts that correspond to one another bear the same reference symbol in each case.

Figure 2:
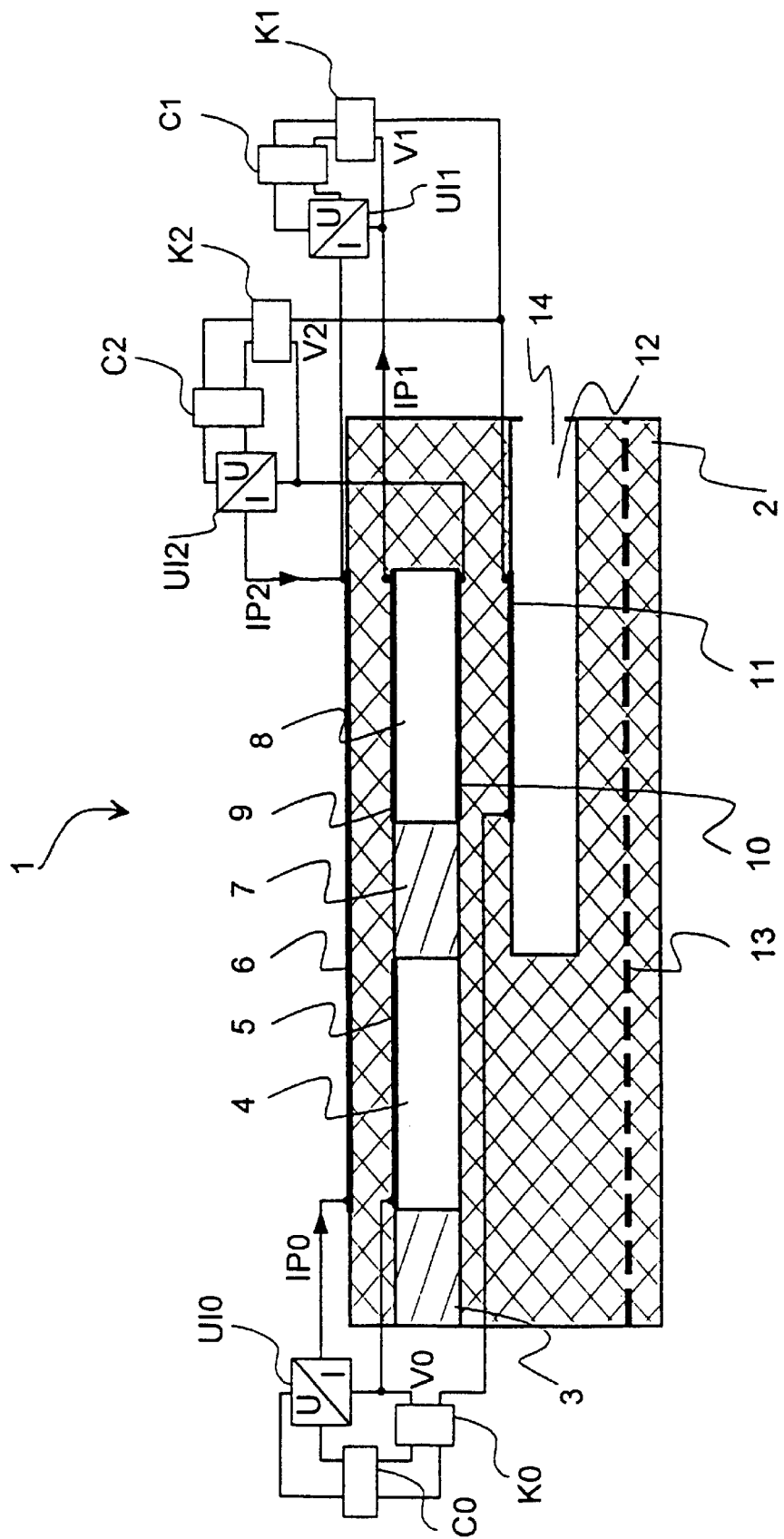
FIG. 2 is a diagrammatic and partially sectional illustration through a NOx measurement sensor and a schematic of a circuit including the NOx measurement sensor according to the invention.

Referring now to the figures of the drawings in detail and first, particularly to FIG. 2 thereof, there is shown a schematic illustration of a section through a NOx measurement sensor 1. The measurement sensor 1 is used in the apparatus illustrated in FIG. 1 as a measurement sensor 1 for determining the NOx concentration in the exhaust-gas tract 27 of an internal combustion engine 20. The measured values from the NOx measurement sensor 1 are read by a control unit 23 that is connected to the NOx measurement sensor 1 and are fed to the operational controller 25 of the internal combustion engine 20. The operational controller 25 drives a fuel feed system 21 of the internal combustion engine 20 such that a NOx-reducing catalytic converter 28, located upstream of the NOx measurement sensor 24 in the exhaust-gas tract 27 of the internal combustion engine 20, exhibits optimum operating behavior.

The measurement sensor 1 is illustrated in more detail in FIG. 2. The measurement sensor 1 is composed of a solid-state electrolyte, for example, $ZrO_2$. The measurement sensor 1 senses the exhaust gas that is to be measured and whose NOx concentration is to be determined through a diffusion barrier 3. The exhaust gas diffuses through the diffusion barrier 3 into a first measurement cell 4.

A Nernst voltage V0 is measured between a first electrode 5 and a reference electrode 11 that is exposed to the ambient air in order to determine the oxygen content in the measurement cell 4. The detection of the Nernst voltage V0 will be described in more detail below. The reference electrode 11 is disposed in an air duct 12 into which ambient air passes through an opening 14.

Using the Nernst voltage V0 as a reference variable, an 8-bit microcontroller serving as a digital controller C0 regulates a voltage-controlled current source UI0 through a setting voltage. The voltage-controlled current source UI0 drives a first oxygen ion pump current IP0 through a solid-state electrolyte 2 of the measurement sensor 1 between the first electrode 5 and an external electrode 6.

The above described circuit configuration thus establishes a predetermined oxygen concentration in the first measurement cell 4.

The second measurement cell 8 is connected to the first measurement cell 4 through a further diffusion barrier 7. The gas present in the first measurement cell 4 diffuses through the diffusion barrier 7 into the second measurement cell 8. A second oxygen concentration is established through a circuit configuration (similar to the circuit configuration of the first measurement cell 4) in the second measurement cell 8. To this end, a second Nernst voltage V1 is tapped off between a second electrode 9 and the reference electrode 11. The details relating to tapping off the Nernst voltage V1 will be further explained below. Using the second Nernst voltage V1 as a reference variable, a digital controller C1, which can be implemented, for example, in the 8-bit microcontroller employed for the controller C0, regulates a second voltage-controlled current source UI1 by a second setting voltage. The second voltage-controlled current source UI1 drives a second oxygen ion pump current IP1 out of the second measurement cell 8.

Thus, the second circuit configuration establishes, in the second measurement cell 8, a predetermined oxygen concentration that is different than an oxygen concentration in the first measurement cell 4. The predetermined oxygen concentration is selected such that the processes that proceed do not affect NOx. In particular, no decomposition takes place.

Then, the NOx is pumped from a measurement electrode 10 to the external electrode 6 in a third oxygen ion pump current IP2. The measurement electrode 10 can be a catalytic configuration. The oxygen ion pump current IP2 is carried essentially only by oxygen ions that originate from the decomposition of NOx at the measurement electrode 10 because the residual oxygen content in the second measurement cell 8 has been lowered sufficiently. A third Nernst voltage V2 is tapped off between the measurement electrode 10 and the reference electrode 11 in order to drive the third oxygen ion pump current IP2. The details relating to tapping off the third Nernst voltage V2 will be further explained below. Using the third Nernst voltage V2 as a reference variable, a controller C2 regulates a third voltage-controlled current source UI2 through a third setting voltage. The third voltage-controlled current source UI2 drives the pump current IP2, which is the measure of the NOx concentration in the second measurement cell 8 and, therefore, in the exhaust gas to be measured.

The third circuit configuration drives the pump current of oxygen ions, representing the measurement current, out of the second measurement cell 8.

Figure 3:
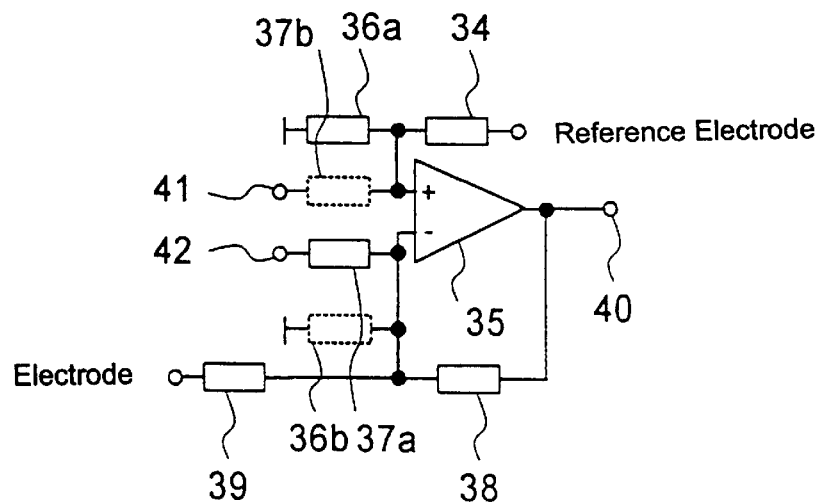
FIG. 3 is a circuit diagram of a conditioning circuit of FIG. 2.

When the respective Nernst voltages V0, V1, V2 are tapped off, they are routed to a respective conditioning circuit that is connected upstream of the respective A/D port of the respective microcontroller. One conditioning circuit is provided for each A/D port. A conditioning circuit is shown in more detail in FIG. 3.

The respective electrode 5, 9, 10 is connected through a resistor 39 to the inverting input of an operational amplifier 35. The connection between the resistor 39 and the inverting input (−) of the operational amplifier 35 is further coupled back through a resistor 38 to the output of the operational amplifier 35. The reference electrode 11 is connected through a resistor 34 to the non-inverting input (+) of the operational amplifier 35. Therefore, an amplified and shifted voltage is present at the output 40. The amplified and shifted voltage results in the following way from the voltage between the electrode and the reference electrode:

$$U = V0 \times G + O.$$

where V0 designates the Nernst voltage, U designates the output voltage, G designates the gain, and O designates the offset shift. Therefore, the circuit transforms a small range of the Nernst voltage into a range of, for example, 0 to 5 V. The small range of the Nernst voltage that is "cut out," lies around the desired value of the Nernst voltage constituting the reference variable.

As a result, using a standard configuration with an 8-bit A/D converter at a maximum voltage of 5 V, a Nernst voltage resolution of 0.4 mV, for example, is achieved by dimensioning the circuit suitably. The resolution is in contrast with a resolution of 20 V that would result if the Nernst voltage were to be measured directly. If the following resistor values are used

| Resistor | Value in $\Omega$ |
|---|---|
| 34 | 20k |
| 36a | 124k |
| 36b | nc |
| 37a | 140k |
| 37b | nc |
| 38 | 1M |
| 39 | 20k | the measurement range is 350 mV to 450 mV.

The resolution of the Nernst voltage in the vicinity of the desired value of the reference variable is increased because only the range of the Nernst voltage that is significant for the regulation is registered. Outside the value, the A/D converter supplies the upper or lower maximum value, but this is not harmful to the control task.

The region around the desired value of Nernst voltage that is amplified by the circuit depends on the dimensioning of the resistors 34, 37a, 37b, 38, and 39. A range of 5 mV to 1 V is advantageous with a gain factor of 5 to 1000.

Depending on whether the resistors 36b and 37b or 36a and 37a(shown in FIG. 3 with dashed and continuous lines, respectively) are used, the offset shift can be set to be positive or negative. The respective voltage across the electrode 5, 9, 10 and, respectively, the reference electrode 11 with respect to the reference of the microcontroller can be tapped off at the output terminals 41 and 42, respectively, of the circuit illustrated in FIG. 3. Such a configuration can be advantageous for testing purposes.

We claim:

1. A circuit for a measurement sensor detecting a NOx concentration in a gas, comprising:

a first measurement cell;

a second measurement cell connected to said first measurement cell, said first and second measurement cells disposed in a solid-state electrolyte;

a first circuit configuration tapping off a first Nernst voltage serving as a first reference variable for establishing an oxygen concentration in said first measurement cell differing from an oxygen concentration in a gas to be measured;

a second circuit configuration tapping off a second Nernst voltage serving as a second reference variable for establishing an oxygen concentration in said second measurement cell differing from an oxygen concentration in said first measurement cell;

a third circuit configuration tapping off a third Nernst voltage serving as a third reference variable for driving a pump current of oxygen ions originating from NOx out of said second measurement cell;

at least one conditioning circuit; and at least one digital controller having at least one control point;

at least one of said first, second, and third Nernst voltages being fed to said at least one controller through said at least one conditioning circuit for shifting and amplifying said at least one of said first, second, and third Nernst voltages such that at said at least one controller at least one of said first, second, and third reference variables lies in a range around said at least one control point of said at least one controller, and a reference potential of a conditioned at least one of said first, second, and third Nernst voltages equals that of said at least one controller.

2. The circuit according to claim 1, wherein said at least one conditioning circuit includes:

an output;

an electrode;

a reference electrode;

an operational amplifier with an operational amplifier output connected to said output, a conditioned at least one of said first, second, and third Nernst voltages being present at said output, an inverting input, and a non-inverting input;

a first resistor connected to said inverting input and to said electrode for tapping off a first potential;

a second resistor connected to said inverting input and to said operational amplifier output;

a third resistor connected to said non-inverting input and to said reference electrode; and a fourth resistor connected to said non-inverting input and to ground.

3. The circuit according to claim 1, wherein said at least one controller has at least one A/D converter converting a conditioned at least one of said first, second, and third Nernst voltages from analog to digital with 8-bit resolution.

* * * * *